United States Patent [19]

Smith

[11] Patent Number: 4,960,423

[45] Date of Patent: Oct. 2, 1990

[54] METHOD OF ENHANCING THE ATTACHMENT OF ENDOTHELIAL CELLS ON A MATRIX AND VASCULAR PROSTHESIS WITH ENHANCED ANTI-THROMBOGENIC CHARACTERISTICS

[76] Inventor: Donald W. Smith, 609 S. Clinton St., Baltimore, Md. 21224

[21] Appl. No.: 442,458

[22] Filed: Nov. 17, 1982

[51] Int. Cl.$^5$ ........................... A61F 2/06; A61F 2/02
[52] U.S. Cl. .......................................... 623/1; 623/11; 623/15
[58] Field of Search .................... 428/36; 3/1, 1.4, 1.5; 128/335.5; 623/1, 11, 15, 16

[56] References Cited

U.S. PATENT DOCUMENTS

| | | | |
|---|---|---|---|
| 4,187,852 | 2/1980 | Urray et al. | 623/1 |
| 4,329,383 | 5/1982 | Joh | 3/1 X |

OTHER PUBLICATIONS

Clearly et al., Exp. Mo. Pathol. 28, 227 (1978).
Gospodarowicz et al., Proc. Nat'l Acad. Sci. USA, vol. 77, No. 7, 4094-4098.
Medran et al., J. Cell. Bio., vol. 90, 332 338.
Senir et al., J. Acad. Invest., vol. 66, 859-862.
Postlewaite et al., Proc. Natl. Acad. Sci USA, 75, 871 (1978).
Kleinman et al., J. Cell. Bio., 88 473 (1981).
Seppa et al., Cell. Biology, 5, 813 (1981).
Ali et al., Cell, 14 439 (1978).
Partridge; "The Chemistry of Connective Tissues", J. of Biochemistry, 61, 11 (1955).

Primary Examiner—Richard J. Apley
Assistant Examiner—D. Isabella
Attorney, Agent, or Firm—John Lezdey

[57] ABSTRACT

The attachment and growth of endothelial cells on the luminal surface of a vascular prosthesis are enhanced by coating the luminal surface of the vascular prosthesis with peptide derived from elastin. The resultant vascular prosthesis, which may be seeded with endothelial cells just prior to implantation has an enhanced anti-thrombogenic luminal surface.

13 Claims, 1 Drawing Sheet

METHOD OF ENHANCING THE ATTACHMENT OF ENDOTHELIAL CELLS ON A MATRIX AND VASCULAR PROSTHESIS WITH ENHANCED ANTI-THROMBOGENIC CHARACTERISTICS

BACKGROUND OF THE INVENTION

This invention concerns a vascular prosthesis having a luminal surface with anti-thrombogenic characteristics and the method of preparation thereof. More particularly the invention concerns a method for enhancing the attachment and growth of endothelial cells on a matrix, such as a vascular prosthesis and a synthetic vascular prosthesis having a luminal surface, i.e. the blood contacting surface which is provided with an enhancing agent for the attachment of endothelial cells.

Due to continuously improving surgical techniques, the implantation of prosthetic vascular grafts is increasing. However, the clinical usefulness of synthetic vascular prostheses for vascular reconstruction is limited by the tendency of such grafts to thrombogenicity.

An endothelial cell lining within a graft is believed to provide a non-thrombogenic surface. According to recent investigations by Graham et al, Arch. Surg. 115 1289 (1980) and Surgery 91, 550 (1982) and Burkel et al, J. Surg. Res. 30, 305 (1981), improvement in the development of an endothelial lining in dacron and in polytetrafluoroethylene vascular grafts is obtained by seeding the prosthesis with endothelial cells prior to implantation.

It is well known that the substrate is critical to the growth and proliferation of cells. Among the many materials which have been investigated for effectiveness as cell substrates are collage and fibronectin, components of the extracellular matrix and the intact extracellular matrix. The ability of these proteins to promote cell adhesion, growth and motility have been studied in particular by Postlewaite et al, Proc. Natl. Acad. Sci. USA 75, 871 (1978); Kleinman et al, J. Cell Biol. 88, 473 (1981); Seppa et al, Cell. Biol. 5, 813 (1981); Ali et al, Cell. 14, 439 (1978); Klebe, Nature 250, 248 (1974); Gospodarowicz et al, Proc. Natl. Acad. Sci. USA 77, 4094 (1980) and Klebe et al, J. Cell. Physiol. 109, 481 (1981).

The properties, structure and composition of elastin, another protein of the vascular wall have also been investigated extensively, for example, by Partridge et al, Biochem. J. 61, 11 (1955) and Clearly et al, Exp. Mol. Pathol 28, 227 (1978). More recently, the biosynthesis of elastin by ligamentum nuchae fibroblast has been reported by Mecham et al, J. Cell. Biol. 90, 332 (1981); Senior et al, J. Clin. Invest. 66, 859 (1980) have disclosed that elastin derived peptides, produced by digesting elastin with human neutrophil elastase, are chemotactic for human inflammatory cells and the preparation of an elastomer by cross linking a synthetic polytetrapeptide similar to elastin sequences (but not containing desmosines) has been disclosed by Urry et al, J. Biomed. Mat. Res. 16, 11 (1982).

Studies concerning the interaction of endothelial and vascular smooth muscle cells have been reported by Karnovsky Amer. J. Pathol. 105, 200 (1981) and Haudenschild et al, Lab. Inves. 41, 407 (1979).

However, these studies have not yet led to improvements needed in the performance of vascular prostheses, particularly for small vessel prostheses.

SUMMARY OF THE INVENTION

An object of the invention is the provision of an improved vascular prosthesis.

Another object of this invention is the provision of a vascular prosthesis with improved anti-thrombogenic characteristics.

A particular object of the invention is the provision of a vascular prosthesis having a luminal surface with enhanced capability for the attachment and growth of vascular endothelial cells.

A further object of the invention is the provision of a method for enhancing the attachment and growth of vascular endothelial cells on a synthetic matrix.

Another particular object of the invention is the provision of a method for enhancing the attachment and growth of vascular endothelial cells on the luminal surface of a synthetic vascular prosthesis.

The foregoing and other objects are achieved by the invention disclosed below.

It has been discovered that peptides derived from elastin are particularly effective to enhance the attachment and growth of endothelial cells on a synthetic matrix.

According to the method of the invention, the attachment of endothelial cells on the luminal surface of a vascular prosthesis is enhanced by coating the luminal surface with peptides derived from elastin.

The vascular prosthesis of the invention which has improved anti-thrombogenic characteristics is comprised of a matrix suitable for use as a replacement artery or vein having a coating on its luminal surface of a peptide derived from elastin.

BRIEF DESCRIPTION OF THE DRAWINGS

The figure is a group of photomicrographs designated (a) through (d) which show, at a magnification of 250×, the endothelial cell attachment and spreading, after 2 hours, on a matrix coated with (a) a thin film of α-elastin, 6.2 μg./cm/$^2$, (b) a thin film of α-elastin coacervate, 6.2 μg./cm.$^2$, (c) a thin film of K-elastin, 6.2 μg./cm.$^2$ and (d) a thin film of 1% of bovine serum albumin.

DESCRIPTION OF THE INVENTION

Figure 1A:
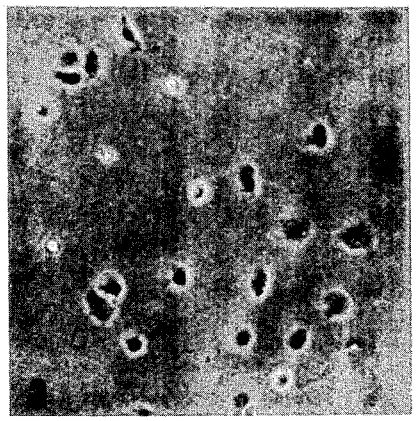
Figure 1B:
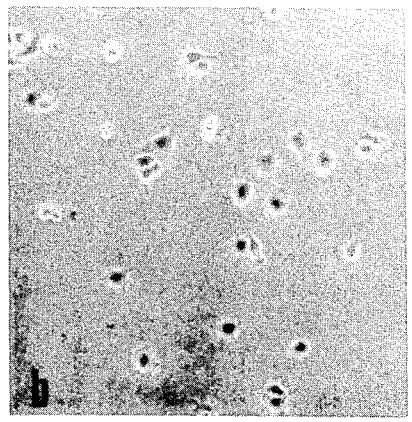
Figure 1C:
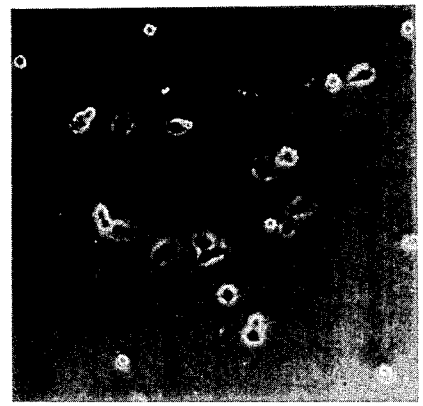
Figure 1D:
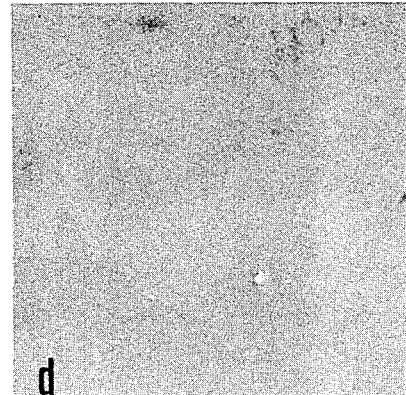

Peptides used to coat the luminal wall of vascular prostheses in accordance with the invention are derived from elastin or a coacervate thereof. The peptides are preferably water soluble peptides obtained by the acid or alkaline hydrolysis of elastin or a coacervate thereof obtained by heating a solution of the peptide rapidly to about 37° C. α-Elastin, which may be obtained from elastin by hydrolysis with oxalic acid, as disclosed by Partridge et al, ibid, has been found to be particularly effective to promote the adhesion and growth of endothelial cells on a synthetic matrix. However, K-elastin which may be prepared by the alkaline hydrolysis and ethanol extraction of bovine ligamentum nuchae elastin, as disclosed by Robert et al, Prot. Biol. Fluids 3, 683 (1968) and the coacervates of water soluble peptides have also been found to promote the adhesion and growth of endothelial cells on a synthetic matrix effectively.

Elastin peptides, which, in accordance with the invention are coated on the luminal wall of a vascular prosthesis are identifiable by the presence in their structure of desmosine, a unique, lysine-derived cross linked amino acid characteristic of elastin, of about 0.06%, and more preferably, by a desmosine content of about 0.53%, and are also identified by their amino acid composition.

According to the invention, a vascular prosthesis having an enhanced anti-thrombogenicity is prepared by coating the luminal surface of a matrix useful as a vascular prosthesis with a thin film of a peptide derived from elastin, preferably a water soluble peptide which contains desmosine, such as α-elastin, K-elastin or a coacervate thereof. The film of peptide may be coated by absorbtion on the surface of the matrix or by bonding through a chemical group fixed to the luminal surface of the matrix which is capable of bonding to the peptide.

The resultant thin film contains about 6 to 19 μg./cm.$^2$ and more preferably about 6 μg./cm.$^2$ of the peptide.

The formation of a thin film by absorbtion, in accordance with the invention, is carried out by contacting a solution of the peptide with the luminal surface of the matrix useful as a vascular prosthesis, air drying the luminal surface and, if desired, washing the luminal surface with water or a neutral buffered saline solution to remove any excess peptide.

To prepare a vascular prosthesis having a covalently bound film of elastin peptide on its luminal surface, the peptide is contacted with a matrix useful as a vascular prosthesis having fixed on its luminal surface chemical groups, such as oxygen containing groups, capable of bonding with the elastin peptide. For example, glutaraldehyde a bifunctional reagent is known to bind to the protein surface of an artery or vein through one of the amino groups; the remaining aldehyde groups can react with an elastin peptide to form a Shiff base. The resultant bound peptide is shown by the following formula:

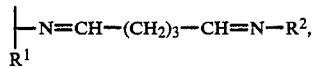

wherein
$R^1$ is the protein surface of a vein or artery and
$R^2$ is an elastin peptide.
Reduction of the Schiff's base results in a stable peptide bond.

Arteries or veins, such as human umbilical veins and bovine carotid arteries can be fixed with glutaraldehyde, by contact with a solution containing about 2.5% of glutaraldehyde and a pH of 7.6 for about 72 hours at ambient temperature, as disclosed by Christie et al., J. Surg. Res. 28, 519 (1980). According to a personal communication of Moczar, arteries and veins can also be fixed with glutaraldehyde by placing the artery or vein in a closed chamber saturated with glutaraldehyde vapor at about 4° C.

Bonding of the elastin peptide to a glutaraldehyde-fixed vein or artery can be carried out by contacting the thus fixed vein or artery with a solution of the elastin peptide and thereafter, reducing the resultant Schiff's base, with a mild reducing agent, such as NaBH$_4$.

Elastin peptides can be covalently bonded similarly to a synthetic polymeric matrix. For example a dacron prosthesis may be coated with a hydrogel of glycol methacrylate, according to Kronick, P. L. in: *Synthetic Biochemical Polymers*, (Szycher and Robinson, editors) Technomic Publishing, Westport, Conn. pp. 153-169, 1st. ed. (1980). In this procedure, free radicals on the plastic surface initiate the polymerization of monomer film as a thin coat on the plastic surface; hydroxyl gourps of the thus attached glycol, when activated by cyanogen bromide can be covalently bonded to the amino group of elastin peptides, as disclosed for example by Porath, Nature 218, 834 (1968). Likewise, hydroxyl groups can be introduced into expanded Teflon using a commercial etching solution called Tetra Etch, the thus etched expanded Teflon can be reacted with potassium permanganate and then bonded to the elastin peptides according to the Porath procedure. Other synthetic matrixes can be bound to the elastin peptide in a similar manner, by chemically introducing oxygen containing groups such as hydroxyl groups, aldehyde groups or carboxylic acid groups onto their surfaces.

In some cases, if desired, catheptic fragments of fibronectin, which do not bind gelatin agarose and endothelial growth factors, can be mixed with elastin peptides and conjugated, bonded or absorbed on the luminal surface of a vascular prosthesis, in accordance with the invention to further enhance endothelial attachment and growth and prevent blood clotting.

A vascular prosthesis of the invention having elastin peptides absorbed or bonded on its luminal surface may be seeded with endothelial cells, as disclosed for example by Graham, et al, ibid and Burkel et al, ibid, most desirably, just prior to implantation.

The following examples further illustrate the best mode currently contemplated for carrying out the invention, but the illustrative examples must not be considered as limiting the invention in any manner.

EXAMPLES

Preparation of Elastin Peptides

α-Elastin was prepared by the oxalic acid hydrolysis of autoclaved bovine aortic elastin, as described by Partridge et al, ibid. The resultant peptide had the following amino acid composition in percent by weight.

| | |
|---|---|
| Hydroxyproline | 1.22 |
| Aspartic acid | 0.49 |
| Threonine | 0.93 |
| Serine | 0.94 |
| Glutamic acid | 2.09 |
| Proline | 12.0 |
| Glycine | 27.4 |
| Alanine | 29.3 |
| Valine | 12.3 |
| Isoleucine | 2.24 |
| Leucine | 5.28 |
| Tyrosine | 1.24 |
| Phenylalanine | 2.47 |
| Isodesmosine | 0.22 |
| Desmosine | 0.31 |
| Lysino-Norleucine | 0.51 |
| Lysine | 0.46 |
| Arginine | 0.60 |
| | 100% |

K-elastin was prepared by alkaline hydrolysis and ethanol extraction of bovine ligamentum nuchae elastin according to Robert et al, ibid.

A coacervate was prepared by rapidly heating an aqueous solution of the peptide to 37° C.

αElastin-DAP (α-elastin-diaminopentane) was prepared by dissolving α-elastin in thionyl chloride and then reacting the resultant composition with diaminopentane.

Preparation of Substrates

Solutions containing 12.5 μg/25 μl or 37.5 μg/75 μl of α-elastin, K-elastin, a coacervate of α-elastin or α-elastin-DAP were placed in 16 mm wells of Costar Cluster tissue culture dishes and air dried in a laminar flow hood overnight. All peptides were in aqueous solution, except for a sample of elastin-DAP which was in dimethyl sulfoxide (DMSO). Control and treated substrates were prepared by treatment with 250 μl of a 1% heat-activated solution of bovine serum albumin (BSA) for 10 min. to eliminate non-specific attachment in the manner of Klebe et al, ibid. The substrates were rinsed twice with modified Medium 199 before applying the cells.

Cell Culture

Endothelial cells were harvested from human umbilical veins by perfusion of the intimal lining with a 1 mg/ml solution of collagenase as described by Gimbrone et al, J. Cell Biol. 60, 673 (1974) and Jaffe et al, J. Clin. Inves. 52, 2745 (1973). The cells were cultured in Medium 199 supplemented with 20% fetal calf serum, 15 mM HEPES (N-2-hydroxyethylpiperazine-N'-2-ethanesulfonic acid), pH 7.2, $10^{-6}$ M thymidine, 0.25 mcg./ml. amphotericin-B, and 50 ug./ml. gentamicin. Confluent cultures were treated with 0.025% trypsin—0.05% EDTA in $Ca^{++}$ $Mg^{++}$-free saline to release cells prior to adhesion assays.

Cell Adhesion

Cell adhesion assays were carried out with secondary cultures of endothelial cells. The cells were released from tissue culture flasks with trypsin—EDTA and resuspended in Med. 199 without serum. The cells were plated at a concentration of $3 \times 10^{-4}$ cells/16 mm well of 24-well Costar Cluster tissue culture dishes which had been treated with elastin peptides. After 2 hours, non-adherent cells were removed with two rinses of Med. 199, and the attached cells were freed with trypsin and counted in an electronic particle counter (Coulter Electronics). Adhesion was expressed as the percent of plated cells which had attached.

The results of the cell adhesion assays are shown in Table 1.

TABLE 1

| Ex. | Peptide Type | % Adhesion* μg/cm² peptide 6.2 | % Adhesion* μg/cm² peptide 18.6 | Degree of Cell Spreading |
|---|---|---|---|---|
| (a) | α-elastin | 34 | 33 | extensive spreading |
| (b) | α-elastin coacervate | 27 | 27 | slight spreading |
| (c) | K-elastin | 20 | 21 | moderate spreading |
| (d) | albumin | 1 | 1 | cells rounded |
| (e) | α-elastin-DAP | 29 | 24 | |

*Average of triplicate determinations

Discussion of Results

As shown in Table 1, both α- and K-elastin peptides substantially increased the adhesion and growth of endothelial cells on a plastic matrix. Examination of the attached cells in the phase microscope indicated that the cells had flattened and spread extensively on the peptide films. Less spreading, with minimal filopodial development occurred on the coacervate surface. These results are also shown in the figure, wherein (a), (b), (c) and (d) correspond to the examples set forth in Table 1.

The foregoing shows clearly that when peptides prepared from insoluble elastin, by chemical hydrolysis were applied to a plastic matrix as a thin film, the adhesion and growth of endothelial cells were significantly increased during the 2 hour assay period. Although cell adhesion was also high when α-elastin was applied as a coacervate or gel, the cells were much less extensively spread, when viewed in the phase microscope. However, the persistence of the ability of the peptide coacervates to enhance the adhesion of endothelial cells is some indication that this ability may involve specific regions of the peptide.

In view of the disclosure of McKeehan et al, J. Cell. Biol. 71 727 (1976), that positively charged surfaces produced by coating with poly-lysine or histones promote cell adhesion and growth, α-elastin was conjugated with diaminopentane, to produce a peptide having a higher positive charge than the initial α-elastin; however, α-elastin-DAP was consistently less effective in promoting the adhesion of endothelial cells than unmodified α-elastin, indicating that in this case at least, a peptide with increased positive charge does not increase the degree of adhesion of cells, over that of the unmodified peptide.

Using a higher concentration of peptide, i.e. 18.6 μg./cm.², compared to 6.2 μg./cm.² had no significant effect on the percent of cell adhesion, which suggests that specific binding sites may have been saturated by the lower amount.

Preparation of an Artery Containing Bound α-Elastin

Bovine carotid arteries are placed in a 2.5% glutaraldehyde solution having a pH of 7.6 for 72 hours at ambient temperature. The arteries are then washed with water and placed in a solution containing an excess of α-elastin having a pH of 7.2 for 24 hours at 4° C. The arteries are washed with water and then suspended in a 0.2 M phosphate buffer having a pH of 7.2. An excess of $NaBH_4$ in amount of 10% of the weight of the arteries is slowly added to the solution containing the arteries over a period of 1 hour. After 12 hours, the reduction is stopped by washing first with 0.5 N acetic acid and then with water. The arteries which thus have a coating of α-elastin fixed on their luminal surfaces, are stored in 50% ethanol until used for endothelial seeding. They can also be lyophilized and sterilized with ethylene oxide and stored until used, as disclosed by Robert et al, Path. Biol. 24. Suppl. 42 (1976).

As an alternative to reduction, the shift bases and excess aldehyde can be treated with lysine.

It is evident that other sources than elastin can be used for the peptides useful in the invention. Thus sources equivalent to elastin are considered within the spirit and scope of the invention. Likewise, peptides other than α-Elastin, K-Elastin (or a coacervate thereof) within the scope and spirit of the invention.

What I desire to protect and claim by Letters Patent is:

1. The combination of a synthetic vascular prosthesis having a blood contacting surface and suitable for use as a replacement artery or vein and a resilient coating on the blood contacting surface of said prothesis of a water soluble peptide derived from elastin and having desmosine as part of the structure capable of enhancing the attachment of endothelial cells to said blood-contacting surface, said prosthesis thus having an enhanced antithrombogenic blood contacting surface.

2. The combination of claim 1 in which said peptide comprises -elastin, or K-elastin.

3. The combination of claim 1 in which said peptide is bonded to said blood contacting surface of said matrix.

4. The combination according to claim 3 in which a bonding agent on said blood contacting surface for bonding said peptide to said matrix.

5. The combination according to claim 4 in which said bonding agent comprises amino groups, or oxygen containing groups selected from aldehyde, carboxylic acid and hydroxyl groups.

6. The combination according to claim 3 in which said prosthesis is comprised of a human or animal vein or artery having a bifunctional aldehyde bonded to said blood contacting surface and said peptide.

7. The combination according to claim 3 in which said prosthesis is comprised of dacron or polytetrafluoroethylene having hydroxyl groups bonded with said peptide and fixing said peptide to said blood contacting surface.

8. The combination of a non-thrombogenic synthetic vascular prosthesis having a blood contacting surface suitable for use as a replacement artery or vein and a resilient coating on the blood contacting surface of said prosthesis consisting essentially of a desmosine comprising elastin, said peptide being capable of enhancing the attachment of endothelial cells to said surface.

9. The combination of claim 8 in which said peptide is covalently bonded to said blood contacting surface of said matrix.

10. The combination according to claim 8 in which said matrix is comprised of a human or animal vein or artery convalently bonded to said blood contacting surface and also covalently bonded to said peptide.

11. The combination of claim 1 in which said peptide is K-elastin obtained by the alkaline hydrolysis of elastin.

12. The combination of claim 1 in which said peptide is a coacervate of $\alpha$-elastin obtained by heating an aqueous solution of $\alpha$-elastin to about 37° C.

13. The vascular prosthesis according to claim 8 in which said matrix is comprised of dacron or polytetrafluoroethylene material having hydroxyl groups fixed to said blood contacting surface which covalently bond with said peptide and fix said peptide to said surface.

* * * * *